(12) United States Patent
Nessbaum et al.

(10) Patent No.: US 7,017,457 B2
(45) Date of Patent: Mar. 28, 2006

(54) SCREWDRIVER WITH SCREW HOLDER

(75) Inventors: Ferdinand Nessbaum, Bettlach (CH); Franco Cicoira, Selzach (CH)

(73) Assignee: Synthes (USA), Paoli, PA (US)

( * ) Notice: Subject to any disclaimer, the term of this patent is extended or adjusted under 35 U.S.C. 154(b) by 0 days.

(21) Appl. No.: 11/002,512

(22) Filed: Dec. 2, 2004

(65) Prior Publication Data

US 2005/0076752 A1    Apr. 14, 2005

Related U.S. Application Data

(63) Continuation of application No. PCT/CH02/00322, filed on Jun. 13, 2002.

(51) Int. Cl.
*B25B 23/10* (2006.01)

(52) U.S. Cl. ...................................... 81/177.85; 81/448
(58) Field of Classification Search .................. 81/436, 81/442, 448, 451, 452, 177.85
See application file for complete search history.

(56) References Cited

U.S. PATENT DOCUMENTS

| 4,060,114 A | | 11/1977 | Matsushima | |
|---|---|---|---|---|
| 4,105,056 A | * | 8/1978 | Arnn | 81/436 |
| 4,899,543 A | * | 2/1990 | Romanelli et al. | 294/103.1 |
| 5,237,893 A | * | 8/1993 | Ryder et al. | 81/452 |
| 5,617,377 A | * | 4/1997 | Perret, Jr. | 24/168 |
| 2001/0022120 A1 | | 9/2001 | Mark et al. | |
| 2003/0164074 A1 | * | 9/2003 | Blackston | 81/451 |

FOREIGN PATENT DOCUMENTS

| DE | 348078 | 1/1922 |
|---|---|---|
| DE | 1775287 | 7/1968 |
| EP | 0 458 449 A1 | 11/1991 |
| FR | 981278 | 5/1951 |

* cited by examiner

*Primary Examiner*—Debra Meislin
(74) *Attorney, Agent, or Firm*—Jones Day

(57) ABSTRACT

A tool is described comprising a shaft having a first longitudinal axis and a front segment, wherein the front segment has a cross-sectional area, wherein the front segment is configured to engage at least a portion of a screw head, and wherein the front segment has at least a first recess having a second longitudinal axis substantially transverse to the first longitudinal axis; at least one spring element housed in the first recess, wherein a first portion of the spring element at least partially protrudes transversely across the first longitudinal axis; wherein the cross-sectional area is substantially polygonal, having a least one radii; wherein the second longitudinal axis is substantially aligned with at least one radii; and wherein the portion of the spring element protruding transversely across the first longitudinal axis is elastically deformable.

18 Claims, 3 Drawing Sheets

SCREWDRIVER WITH SCREW HOLDER

CROSS-REFERENCE TO RELATED APPLICATIONS

This application is a Continuation Application of International Application No. PCT/CH02/00322, filed Jun. 13, 2002, the contents of which are expressly incorporated by reference herein.

FIELD OF THE INVENTION

The invention relates to a screwdriver with a screw holder, as well as to a spring element for use as a screw holder at a screwdriver.

BACKGROUND OF THE INVENTION

So that, during the surgical implantation of an implant, which is to be fastened at a bone, a bone fragment or at a joint of the human or animal body, the surrounding soft parts experience as little damage as possible, it shall be possible to conduct surgery on the bone or, for example, also on a segment of the spinal column without exposing the parts to be treated over a large area (minimal invasive technique). If the openings in the soft parts are very small, non-pointed forceps, for example, are then no longer suitable for introducing bone screws or pedicle screws.

A screwdriver with means for holding a screw is also known from the EP 0 458 449 of RYDER. This known screwdriver comprises a longitudinal shaft part with a free end, which can be introduced into a corresponding recess in a screw head. The elastic means for clamping the screws are inserted into a groove, which is parallel to the longitudinal axis, and consist of a compressible elastomer. Since the elastic means, when in the uncompressed state, protrude radially over at least one side surface of the shaft part, they are compressed when the shaft part is inserted into a complementary recess and press against the side wall of the recess, as a result of which the screw head is held at the shaft part. It is a disadvantage of this development of the elastic means that the boreholes for accommodating the elastic means are configured in a relatively complicated manner and that therefore the screw driver is unsuitable for very small screws.

SUMMARY OF THE INVENTION

The invention is to provide a remedy here. It is an object of the invention to create a screwdriver with an elastic screw holder, which can also be used for the smallest screws.

Pursuant to the invention, this objective is accomplished with a screwdriver with a screw holder, as well as with a spring element for use as screw holder at a screwdriver.

The inventive screwdriver with screw holder comprises essentially a shaft and a spring element, which is disposed transversely to the longitudinal axis. At its rear section, the shaft can be connected with driving means, such as a handle or a machine. The shaft comprises a front segment, which can be introduced into a seat, suitable for a screwdriver, such as a hexagon socket, an internal six-lobe profile, a Phillips (x-shaped) recess or a Torx (6-point star-shaped pattern) at a screw head. The spring element is inserted at the front end of the shaft into a recess with a longitudinal axis directed transversely to the longitudinal axis. The cross-section of the front segment of the shaft is polygonal or star-shaped in the various embodiments of the inventive device, the corners or tips being angular or rounded off and the sides being straight or concave. The longitudinal axis of the recess for the spring element coincides with one of the radii, on which the corners or tips lie. Furthermore, at least on its part protruding beyond the cross section, the spring element can be deformed transversely to the longitudinal axis in the cross-sectional area orthogonal to the longitudinal axis of the shaft.

The advantages, achieved with the invention, can be seen essentially therein that, due to the inventive configuration of the spring element, a small overall depth of the front segment of the shaft is attainable so that screws with heads of low height or with recesses of small depth for accommodating the screwdriver can be used, the front segment of the shaft may be prismatic or cylindrical, as a result of which, in comparison to conical shaft segments, a maximum transfer of force can be exerted on the screw (the so-called "cam out" effect being avoided), the spring element can also be installed subsequently on conventional commercial screw drivers, a screw-holding sleeve is not necessary, so that it is possible to manipulate these screwdriver with one hand, the device can be produced easily, so that a low price is possible and because only a single, radial borehole is required in the front segment of the shaft, the spring element can also be used for the smallest screws and accordingly also for screws in maxillofacial, hand and foot surgery.

In the preferred embodiment of the inventive screwdriver, the recess is constructed as a circular borehole, so that the recess can be produced without great expense also subsequently on conventional, commercial screwdrivers and a spring element can be used.

In a different embodiment of the inventive screwdriver, the recess and the spring element are prismatic in shape. With that, the advantage can be attained that the spring element cannot twist in the recess.

In yet another embodiment of the inventive screwdriver, the spring element is produced from a metallic material, preferably from stainless spring steel or from a superelastic metal, such as Nitinol (nickel-titanium alloy), so that it is suitable for medical application purposes and moreover has a long service life.

In a further embodiment of the inventive screwdriver, the spring element is produced from a plastic, preferably from a thermoplastic material, such as POM. The advantages of a spring element, produced from plastic, lie in the rational manufacturing process (such as injection molding), the low costs and the elimination of the danger of corrosion.

In once again another embodiment of the inventive screwdriver, the spring element has an open slot at its second end, which can be introduced into the seat in a screwdriver. With respect to the cross section of the spring element orthogonal to the longitudinal axis of the recess, this slot is disposed diametrically and divides the spring element at the second end into two cogs, which can be moved elastically and transversely to the longitudinal axis of the shaft. This construction of the spring element permits a maximum holding force to be attained for the screws, which is necessary for surgical applications, so that the danger of the screws being lost in the human body during the surgical intervention can be minimized. Preferably, the dimensions are: between 0.3 mm and 2.0 mm for the diameter of the spring element, between 0.1 mm and 1.5 mm for the width of the slot and between 0.5 mm and 3.0 mm for the length of the slot.

Typically, the dimensions are: between 0.5 mm and 1.5 mm for the diameter of the spring element, between 0.2 mm and 1.2 mm for the width of the slot and between zero 0.8 mm and 2.0 mm for the length of the slot.

Furthermore, the slot may be expanded wedge-shaped towards the outside, that is, towards the end of the spring element protruding over the cross section of the front segment of the shaft, the wedge angle preferably being between 0.1° and 10°. As a result, the advantage can be attained that the stress distribution in the spring element is optimized. As a result, better cushioning properties are achieved and the danger of a fatigue breakage is reduced.

In a different embodiment of the inventive screw driver, the second end of the spring element, protruding over the cross section of the front segment of the shaft, is provided with a taper, so that the cogs, which can be deformed radially and elastically during the insertion of the front segment of the shaft into a corresponding seat for a screwdriver in a screw head, can be compressed more easily transversely to the longitudinal axis of the shaft. The tapering may be present in the form of an obliqueness, a curvature, a bevel or a round edge.

Preferably, the length of the taper, measured parallel to the longitudinal axis of the spring element is 5% to 30% of the diameter of the spring element. Instead of a taper, the second end of the spring element may also have a convex formation.

In yet another embodiment of the inventive screwdriver, the latter comprises several spring elements, which can be inserted in several recesses at the front segment of the shaft. The longitudinal axes of the recesses preferably lie on one of the radii, intersecting the corners or curvature of the cross-sectional area of the front segment of the shaft, orthogonally to the shaft. Due to the use of several spring elements, the holding force, which can be exerted on the head of the screw head, can be increased appreciably for the screw on the screwdriver.

In a further embodiment of the inventive screwdriver, the recess has a ledge at a depth T, measured from the corner or tip, the depth T being equal to or greater than the length of the spring element, which is parallel to the longitudinal axis of the spring element, so that the spring element does not protrude beyond the tip, corner or curvature of the front segment of the shaft. By these means, it can be avoided that the spring element is pushed further into the recess as the front segment of the shaft is inserted into the seat for the screwdriver at the screw head.

Further advantageous developments of the invention are characterized in the dependent claims.

BRIEF DESCRIPTION OF THE DRAWINGS

The invention and further developments of the invention are described in even greater detail in the following by means of partly diagrammatic representations of several examples. In the drawings.

DETAILED DESCRIPTION OF THE INVENTION

Figure 1:
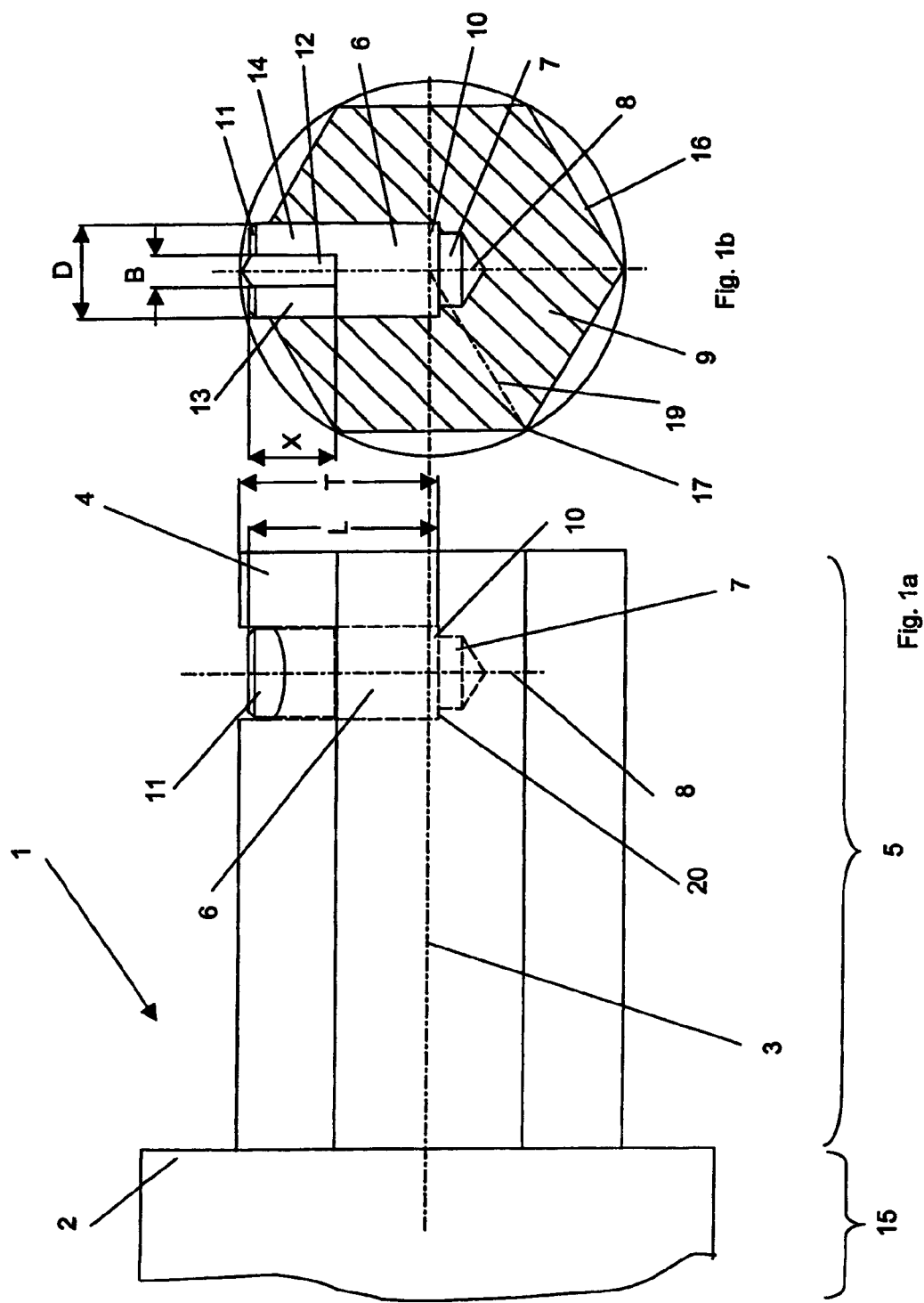
FIG. 1a shows a longitudinal section through an embodiment of the inventive screwdriver with screw holder.
FIG. 1b shows a cross section through the embodiment of the inventive screwdriver with screw holder, shown in FIG. 1a, FIG. 2 shows a cross section through a different embodiment of the inventive screwdriver with screw holder.

The screwdriver 1 with screw holder, shown in FIGS. 1a and 1b, comprises essentially a longitudinal shaft 2 with a longitudinal axis 3, a rear segment 15 of the shaft and a front segment 5 of the shaft, and a spring element 6 with a diameter D. The front segment 5 of the shaft has a hexagonal cross-sectional area 9, which is orthogonal to the longitudinal axis 3 and has straight side 16 and corners 17 and can be inserted into a seat at a screw head, which is suitable for screwdrivers. At the front segment 5 of the shaft, the spring element 6 is pressed into a longitudinal recess 7 in the form of a circular borehole with a longitudinal axis 8, which is perpendicular to the longitudinal axis 3. The six corners 17 of the cross sectional area 9 lie on six radii 19, the longitudinal axis 8 coinciding with one of the radii 19. Adjacent to the corners 17, the spring element 6 protrudes over the adjoining side 16. So that the spring element 6 cannot be pressed into the recess 7 as the front segment 5 of the shaft is being inserted into the seat at a screw head for accommodating a screw driver, there is an axial ledge 20, on which the first end 10 of the spring element 6 rests, in the recess 7.

Furthermore, the spring element 6 comprises a slot 12, having a width B and a length X and passing from the second end 11 of the spring element 6 into the latter. The slot 12 passes through the spring element 6 diametrically and is disposed parallel to the longitudinal axis 8 of the recess 7. The second end 11 of the spring element 6 is divided by the slot 12 into two cogs 13; 14, which are parallel to the longitudinal axis 8 and can be deformed elastically and transversely to the longitudinal axis 8 and towards the edge of the cross sectional area 9, that is, can be deflected towards the longitudinal axis 8. The length L of the spring element 6 is less than the depth T, which extends from the tip 17 up to the ledge 20, so that the spring element 6 is deeper at the tip 17 than at the cross section 9.

Figure 2:
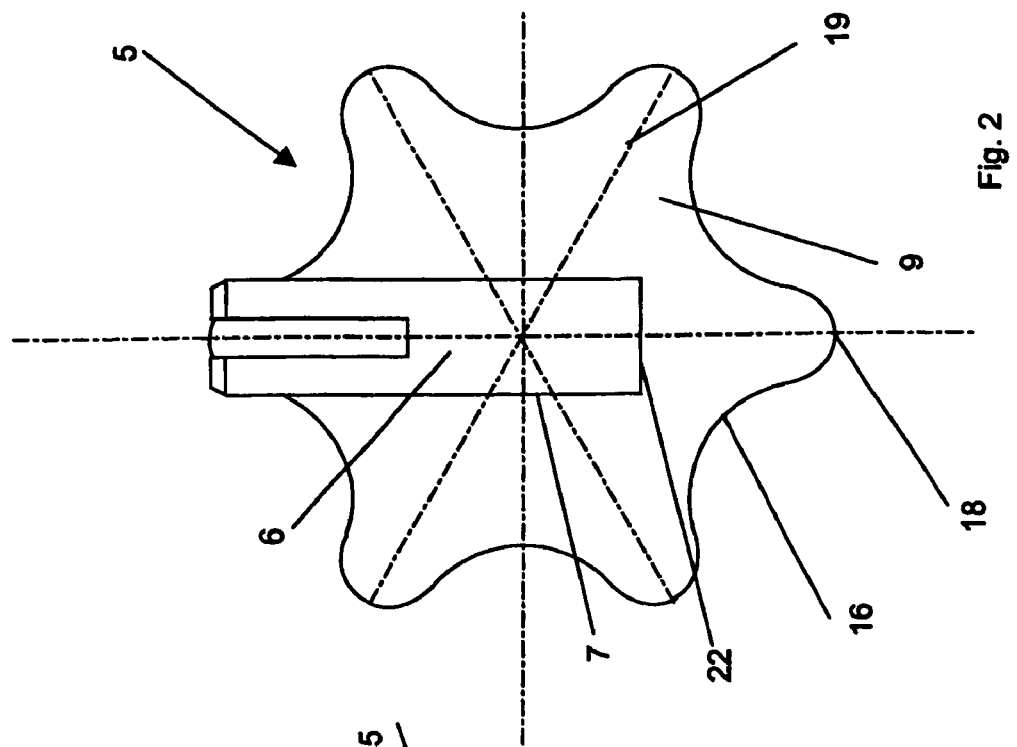

The embodiment of the inventive screwdriver 1, shown in FIG. 2, differs from the embodiment, shown in FIGS. 1a and 1b, only in that the cross-section 9 of the front segment 5 of the shaft is star-shaped. The tips 18 of the cross-section 9, lying on the radii 19, are rounded off convexly and the sides 16, lying between the tips 18, are rounded off concavely. Adjacent, the spring element 6 rests on the base 22 of the borehole 7.

Figure 3:
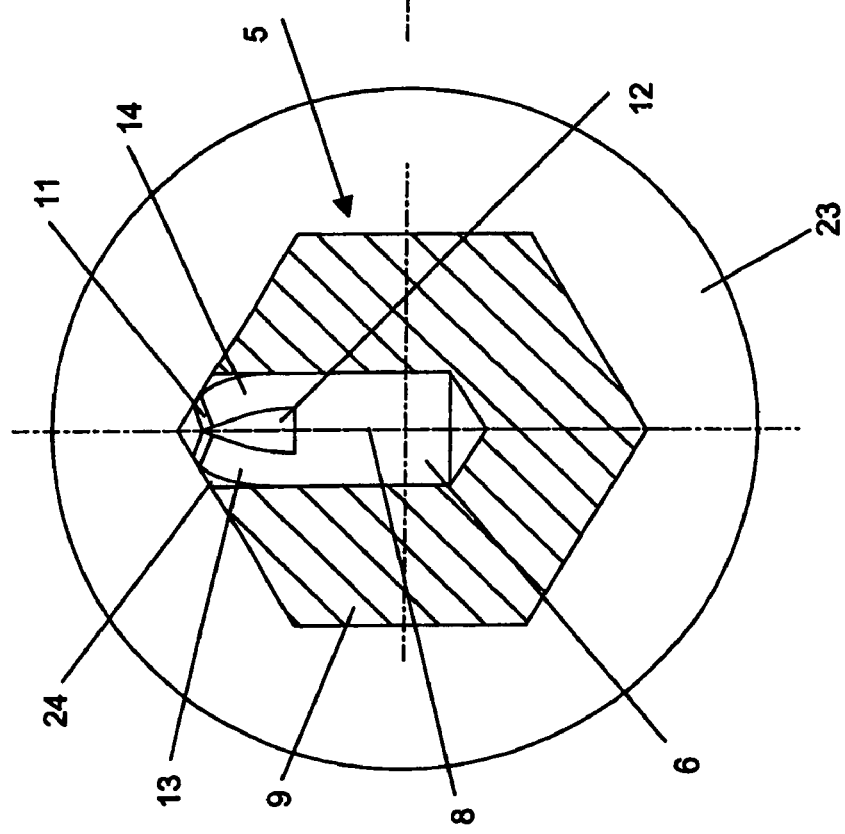
FIG. 3 is a cross section through the embodiment of the inventive screwdriver, shown in FIGS. 1a and 1b, with a front shaft segment, introduced into a recess for accommodating screwdrivers at a screw head.

FIG. 3 shows the front segment 5 of the shaft of the embodiment of the inventive screwdriver shown in FIGS. 1a and 1b, when the latter is introduced into a seat 24 for the screwdriver at a screw head 23. The second end 11 of the spring element 6 is then enclosed completely in the cross section 9. The two cogs 13; 14, which can be deformed elastically, are pressed against the longitudinal axis 8. So that the two cogs 13; 14 can be deformed adequately and do not touch one another at the longitudinal axis 8, the depth T of the recess 7 (FIG. 1a) and the dimensions of the spring element 6, that is, the diameter D and the length L and the width B of the slot 12 (FIG. 1a) must be matched to one another so that, on the one hand, the deformation of the cogs 13; 14 exerts a sufficiently high clamping force on the side walls of the seat 24 and, on the other, the cogs 13; 14 do not hinder the deformation.

Figure 4:
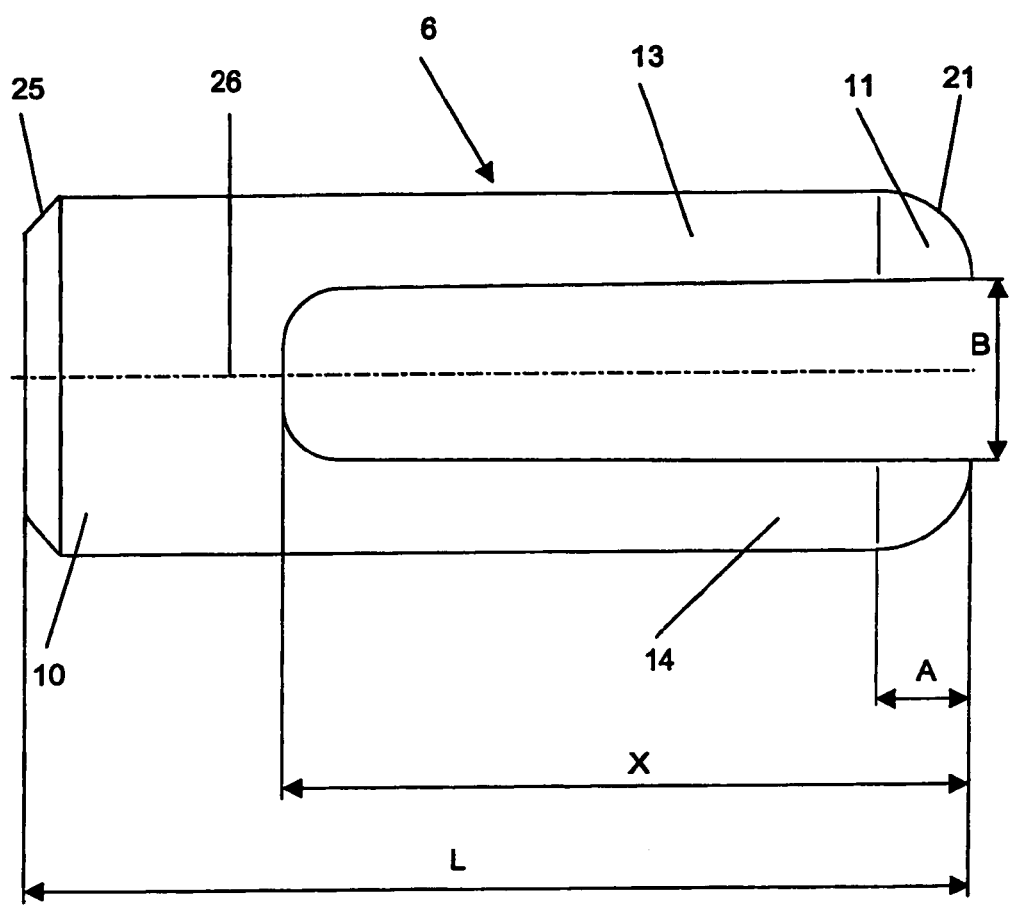
FIG. 4 is a side view of an embodiment of a spring element.

In FIG. 4, an embodiment of the inventive spring element 6 is shown, which is to be used as a screw holder at a screwdriver. The spring element 6 is circular, has a longitudinal axis 26 and comprises, at its first end 10, an obliqueness 25, as well as a convexly rounded tapering 21 at its second end 11, which has a length A, measured parallel to the longitudinal axis 26. In the embodiment shown here, the ratio of the length A of this tapering 21 to the diameter D of the spring element 6 is 1:4, whereas the ratio of the depth X of the slot 12 to the length L of the spring element 6 is 3:4. At the front end 11 of the spring element 6, the slot 12 has a width B and expands in the direction of the front end 11 of the spring element 6 at a wedge angle of 2°. The ratio of the width B to the diameter D is 1:2 here. The two cogs 13; 14 are elastically deformable perpendicularly to the longitudinal axis 8 of the recess 7 (FIG. 1a), the spring forces being determined by the diameter D of the spring element 6 and the dimensions of the slot 12.

What is claimed:

1. A tool comprising:
   a shaft having a first longitudinal axis and a front segment, wherein the front segment has a cross-sectional area, wherein the front segment is configured to engage at least a portion of a screw head, and wherein the front segment has at least a first recess having a second longitudinal axis substantially transverse to the first longitudinal axis;
   at least one spring element housed in the first recess, wherein a first portion of the spring element at least partially protrudes transversely across the first longitudinal axis;
   wherein the cross-sectional area is substantially polygonal, having a least one radii;
   wherein the second longitudinal axis is substantially aligned with at least one radii;
   wherein the portion of the spring element protruding transversely across the first longitudinal axis is elastically deformable; and
   wherein the spring element has a second portion comprising at least two cogs configured to be elastically deformed substantially transversely to the second longitudinal axis.

2. The tool of claim 1, wherein the two cogs are located substantially away from the portion of the spring element at least partially protruding transversely across the first longitudinal axis.

3. The tool of claim 1, wherein the spring element further comprises a slot located between at least two cogs.

4. The tool of claim 3, wherein the slot is wedge-shaped.

5. The tool of claim 1, wherein at least one cog is substantially wedge-shaped.

6. The tool of claim 1, wherein the second portion comprises a second end, and wherein the second end has a taper.

7. The tool of claim 1, wherein the first recess is substantially cylindrical.

8. The tool of claim 1, wherein the first recess is a prismatic cavity.

9. The tool of claim 1, wherein the spring element is comprised of metal.

10. The tool of claim 1, wherein the spring element is comprised of plastic.

11. The tool of claim 1, further comprising a second recess configured to house a spring element.

12. The tool of claim 1, wherein at least one spring element is configured to retain a screw.

13. The tool of claim 1, wherein the spring element has a diameter between about 0.3 mm and about 2 mm.

14. The tool of claim 1, wherein the spring element further comprises a slot, and wherein the slot has a width between about 0.1 mm and about 1.5 mm.

15. The tool of claim 1, wherein the spring element further comprises a slot, and wherein the slot has a length between about 0.5 mm and about 3 mm.

16. The tool of claim 1, wherein the first recess further comprises a ledge configured to prevent the actuation of the spring element into the first recess as the first segment of the tool engages a screw head.

17. The tool of claim 1, wherein the cross-sectional area is substantially hexagonal.

18. The tool of claim 1, wherein the cross-sectional area is substantially star-shaped.

* * * * *

UNITED STATES PATENT AND TRADEMARK OFFICE
CERTIFICATE OF CORRECTION

PATENT NO. : 7,017,457 B2 Page 1 of 1
APPLICATION NO. : 11/002512
DATED : March 28, 2006
INVENTOR(S) : Nussbaum et al.

It is certified that error appears in the above-identified patent and that said Letters Patent is hereby corrected as shown below:

Title page, item (75) Inventors: Delete "Nessbaum" and substitute therefor --Nussbaum--.

Signed and Sealed this

Eleventh Day of July, 2006

JON W. DUDAS
*Director of the United States Patent and Trademark Office*